United States Patent
[19]

Morales

[11] Patent Number: 6,159,173
[45] Date of Patent: Dec. 12, 2000

[54] SPORTS FOREFOOT JOINT STABILIZER

[76] Inventor: Louis Morales, 2338 W. Taylor St., Chicago, Ill. 60612

[21] Appl. No.: 09/064,956

[22] Filed: Apr. 22, 1998

[51] Int. Cl.$^7$ .............................. A61F 13/00; A61F 5/37
[52] U.S. Cl. ............................................. 602/30; 128/882
[58] Field of Search .................... 602/30, 31, 1, 602/5, 60, 61, 66, 75, 19, 65; 128/882, 876, 893; 36/94, 11.5

[56] References Cited

U.S. PATENT DOCUMENTS

| | | | |
|---|---|---|---|
| 353,910 | 12/1886 | Zacharie | 602/30 |
| 1,351,248 | 8/1920 | Hill | 602/66 |
| 1,494,253 | 5/1924 | Karrer et al. | 36/11.5 |
| 1,566,063 | 12/1925 | Barry | 602/30 |
| 1,874,737 | 8/1932 | Boisselier | 602/30 X |
| 2,572,152 | 10/1951 | Horlacher | 602/30 |
| 3,452,748 | 7/1969 | Caprio | 602/19 |
| 3,508,544 | 4/1970 | Moore et al. | 602/65 |
| 3,556,091 | 1/1971 | Haig | 602/30 |
| 3,722,113 | 3/1973 | Birkenstock | 36/9 R |
| 4,751,784 | 6/1988 | Petker et al. | 36/11.5 |
| 5,484,392 | 1/1996 | Sydor et al. | 602/5 |
| 5,840,053 | 11/1998 | Roth | 602/66 |

FOREIGN PATENT DOCUMENTS

| | | | |
|---|---|---|---|
| 640572 | 5/1962 | Canada | 602/30 |
| 416629 | 10/1910 | France | 602/66 |
| 200001 | 7/1923 | United Kingdom | 602/30 |

*Primary Examiner*—Danton D. DeMille
*Assistant Examiner*—Denise Pothier
*Attorney, Agent, or Firm*—Steven C. Repel, Atty

[57] ABSTRACT

A forefoot bandage that is substantially symmetric about a transverse axis and has two notches on opposite ends for positioning on the right and left foot. The notches and angled portions located along the bandage conform to the forefoot to increase comfort, strength and stability. During use, one of the notches of the bandage is placed in the sulcus between the great toe and the second toe of the user and the bandage is then wrapped about the plantar region of the foot near the toes and to support the joints of the great toe and forefoot.

1 Claim, 1 Drawing Sheet

SPORTS FOREFOOT JOINT STABILIZER

BACKGROUND OF THE INVENTION

FIELD OF THE INVENTION

This invention relates to a foot bandage that is ergonomically designed to stabilize the great toe joint and forefoot joints during movement. The bandage has two cut outs or 'notches' placed so as to allow the same bandage to be used on either the right or left foot. In use, the bandage is wrapped about the plantar region of the foot near the toes, with one or two of the notches positioned in the sulcus between the great toe and the second toe.

BACKGROUND INFORMATION

For years, athletes have wrapped their feet in an effort to provide support, stability, and prevent injury. Wrappings tend to keep the great toe joint and forefoot joints in their proper positions, which allow these joints to better endure forward joint movement. Wrapping the foot also lends additional tensile forefoot strength to the tendons and joint capsules. It can be used to splint fractures, to narrow the forefoot, and after bunion surgery.

Bandages have come in all shapes and sizes. Some bandages have been a simple wrap of tape and cloth, others have been more durable, being made of plastic. However, most bandages have interfered with the athlete's shoes due to the bandage's bulk. The bulk has also made the bandages uncomfortable to wear, and therefore, impinged on the athlete's performance. The prior art bandages often interfered with the circulation of the user because of the uneven tension caused by the bandage in combination with the bandage's bulk.

The advantage of the present bandage is that it can be worn longer (up to 24 hours or more) than other bandages because of increased circulation to the toes, it is less bulky. The bandage acts more like a splint than a bandage and is generally made of a rubber material rather than cloth.

SUMMARY OF THE INVENTION

The present invention is a forefoot bandage, ergonomically shaped to comfortably wrap about the user's great toe and forefoot. The invention comprises an ergonomically shaped, durable, rubber-like, flexible membrane having a notch placed near either end, one notch for use on the right foot and one notch for the left foot. In use, each notch fits in the sulcus of the respective foot between the great toe and the second toe. The long end extends arcuately from the notch and is then criss-cross wrapped over the great toe joint, about the top and bottom of the foot, and extending again over the top of forefoot or wrapped around the great toe joint again. The bandage is then secured with electric tape or similar means.

Thus, the object of the invention is to provide the user with a comfortable stabilizer to wear during athletic performance to support the joints of the great toe and the forefoot generally. The invention accomplishes these objects and solves the problems and shortcomings of the prior art in an inexpensive and simple manner. The present invention represents a significant improvement over the prior art in the following ways.

First, the present invention has an ergonomic shape that complements the shape of the user's foot. During use, the bandage remains flat and conforming to the foot, with little or no movement due to the tension of the rubber-like material against the skin and the ergonomic shape of the bandage. The bandage has two arcuate angles in its shape, each at approximately one-third from either end. The arcuate angles allow the bandage to conform to the foot, specifically, at the point that the bandage extends from the sulcus, around the great-toe joint and around the sole of the foot. The result is that the bandage is positioned about the forefoot in a horizontal manner.

Second, the invention significantly increases comfort because the bandage is not likely to bundle-up under the foot during use. Also, the bandage does not interfere with shoewear because of the ergonomic nature of the bandage.

As can be seen, the present invention provides not only increased comfort, but also provides the user's foot with increased strength and stability.

BRIEF DESCRIPTION OF THE DRAWINGS

For a further understanding of the nature and objects of the invention, reference should be had to the following detailed description, taken in conjunction with the accompanying drawing, in which like parts are given like reference numerals and wherein.

DETAILED DESCRIPTION OF THE PREFERRED EMBODIMENT

Figure 1:
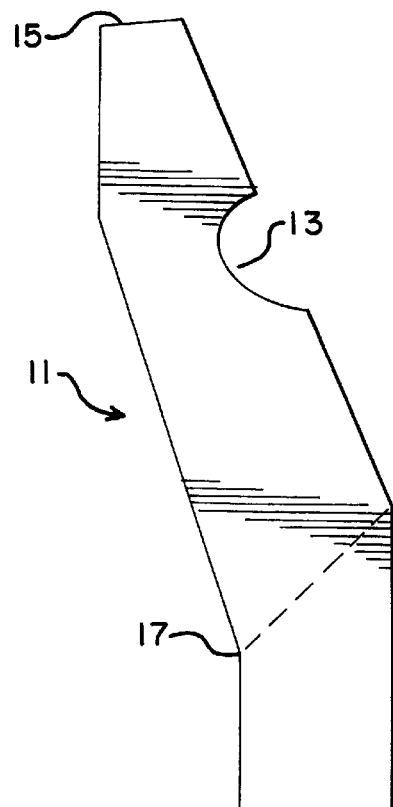
FIG. 1 illustrates a top view of the preferred embodiment of the ergonomic forefoot bandage.

FIG. 1 best illustrates the preferred embodiment of the present invention designated generally by the number 11. In FIG. 1 there can be seen an ergonomic forefoot bandage 11 made of a rubber-like or similar material having two notches 12 and 13, one at the left end 14 and one at the right end 15; and angle each positioned approximately one-third the length from either end 14 and 15.

In the best mode, the device 11 is generally about one and one half inches wide. However, the device 11 could be made wider to accommodate a wider foot or a longer foot.

Figure 2:
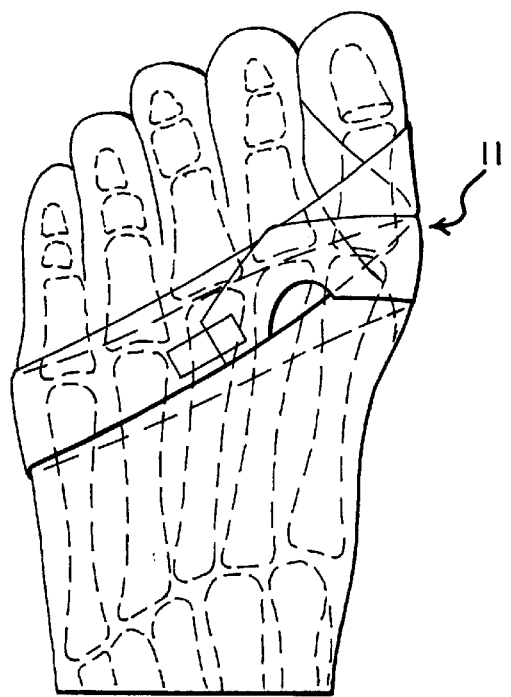
FIG. 2 illustrates a top view of the preferred embodiment of the ergonomic forefoot bandage in use using a single wrap.

FIG. 2 best illustrates the preferred embodiment of the present invention in use about a user's left foot. The left notch 12 is located in the sulcus between the great toe and the second toe. The left end 14 is located under the great toe and is kept in place by the length of the bandage 11 being wrapped over it or taped to the foot. The right end 15 is extended over the great toe joint, about the forefoot in a manner as to have the bandage 11 flush and in alignment with the first joint of the user's toes, and around the sole. The right end 15 is then secured to the body of the bandage 11 near the great toe joint with athletic tape or other suitable attachment means, as in FIG. 2, or the end 15 can be wrapped around the great toe joint again for more stability, see FIG. 3.

Figure 3:
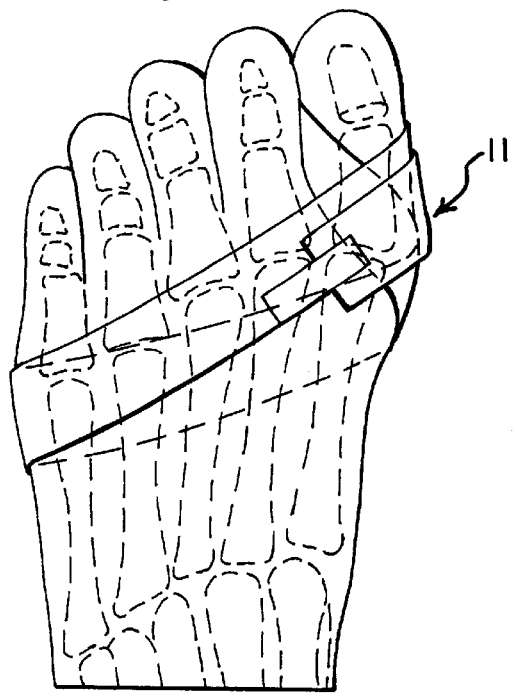
FIG. 3 illustrates a top view of the preferred embodiment of the ergonomic forefoot bandage in use using a double wrap.

FIG. 3 best illustrates the preferred embodiment of the present invention in use about a user's left foot using a double wrap. The double wrap provides increased support to the great toe joint by continuing to extend the right end 15 back through the sulcus and about the great toe joint a second time. The splint 11 is tighter and thicker about the great toe joint and, thus, provides great support.

It should now be apparent that the invention described above possesses all of the attributes set forth in the Specification under the heading 'Summary of the Invention'. Because the invention can be modified to some extent without departing from its principles and intent, the present invention should be understood as encompassing all modifications within the spirit and scope of the following claims.

What I claim is:

1. A device for wrapping a human user's forefoot to stabilize the great toe joint and forefoot, the device comprising a forefoot splint made of a flexible membrane which is elongated and substantially symmetric about its transverse axis having two notches and a left and a right end, one of the notches positioned near the left end and one positioned near the right end; and the forefoot splint further having a left and right portion, the left portion angled at approximately one third the length of the forefoot splint from the left end and the right portion angled at approximately one third of the length of the forefoot splint from the right end such that the splint fits ergonomically about the user's forefoot and at least one of the notches is positioned in the sulcus between the great toe and the second toe when in use.

* * * * *